(12) United States Patent
Miller et al.

(10) Patent No.: US 7,320,416 B2
(45) Date of Patent: Jan. 22, 2008

(54) SHELVING SYSTEMS AND HOLDERS FOR FLEXIBLE BAGS FOR CONTAINING FLUID FOR USE IN FLUID DISPENSING SYSTEMS

(75) Inventors: William A. Miller, Buffalo Grove, IL (US); Christopher Khoo, Lake in the Hills, IL (US)

(73) Assignee: Fluid Management Operations LLC, Wheeling, IL (US)

( * ) Notice: Subject to any disclaimer, the term of this patent is extended or adjusted under 35 U.S.C. 154(b) by 107 days.

(21) Appl. No.: 11/114,371

(22) Filed: Apr. 26, 2005

(65) Prior Publication Data

US 2006/0237480 A1    Oct. 26, 2006

(51) Int. Cl.
B65D 47/00 (2006.01)
(52) U.S. Cl. ................. 222/476; 141/271
(58) Field of Classification Search ............ 222/95, 222/105, 144, 183, 476, 529, 544, 526, 533, 222/132; 141/271–273; 239/106, 110, 112
See application file for complete search history.

(56) References Cited

U.S. PATENT DOCUMENTS

| | | | |
|---|---|---|---|
| 4,341,328 A * | 7/1982 | Redick, Jr. | 222/83.5 |
| 4,871,262 A | 10/1989 | Krauss et al. | |
| 5,622,692 A | 4/1997 | Rigg et al. | |
| 5,673,817 A * | 10/1997 | Mullen et al. | 222/94 |
| 5,785,960 A | 7/1998 | Rigg et al. | |
| 6,273,298 B1 | 8/2001 | Post | |
| 6,398,513 B1 | 6/2002 | Amsler et al. | |
| 6,510,366 B1 | 1/2003 | Murray et al. | |
| 6,540,486 B2 | 4/2003 | Amsler et al. | |
| 6,561,383 B1 * | 5/2003 | Reddy et al. | 222/1 |
| 6,945,431 B2 | 9/2005 | Miller | |
| 6,945,689 B2 | 9/2005 | Armendariz et al. | |
| 6,945,690 B2 | 9/2005 | Armendariz et al. | |
| 6,953,279 B2 | 10/2005 | Midas et al. | |
| 6,955,465 B2 | 10/2005 | Machacek et al. | |
| 6,960,012 B1 | 11/2005 | Biber | |
| 2005/0087545 A1 * | 4/2005 | Engels et al. | 222/1 |
| 2005/0205154 A1 | 9/2005 | Cleveland et al. | |
| 2005/0210834 A1 | 9/2005 | Kamineni | |
| 2005/0211660 A1 | 9/2005 | Galownia et al. | |

(Continued)

FOREIGN PATENT DOCUMENTS

DE    4110299 C1    2/1993

(Continued)

OTHER PUBLICATIONS

International Search Authority, "International Preliminary Report on Patentability and Written Opinion of the International Searching Authority", Nov. 8, 2007, 5 Pages.

Primary Examiner—Lien M. Ngo
(74) Attorney, Agent, or Firm—Miller, Matthias & Hull

(57) ABSTRACT

An improved holder for pivotally supporting a flexible bag containing a liquid component is disclosed for use in a multiple fluid dispensing system. The holder supports the bag in an upright position for space efficiency as well as for dispensing efficiency. An improved shelving system for pivotally supporting a plurality of holders in a compact row and in an upright dispensing position is also disclosed. An improved dispensing system incorporating the disclosed shelving system and flexible bag holder is also disclosed.

15 Claims, 2 Drawing Sheets

U.S. PATENT DOCUMENTS

| | | |
|---|---|---|
| 2005/0211661 A1 | 9/2005 | Galownia et al. |
| 2005/0213426 A1 | 9/2005 | Midas et al. |
| 2005/0217755 A1 | 10/2005 | Vargas |
| 2005/0218149 A1 | 10/2005 | Walsh et al. |
| 2005/0218166 A1 | 10/2005 | Mehan |
| 2005/0232731 A1 | 10/2005 | Lund |

FOREIGN PATENT DOCUMENTS

| | | |
|---|---|---|
| EP | 0443741 B1 | 6/1995 |
| EP | 1276670 B1 | 9/2005 |
| EP | 1417024 B1 | 9/2005 |
| EP | 1580151 A1 | 9/2005 |
| EP | 1214566 B1 | 10/2005 |
| JP | 2005-153938 A | 6/2005 |
| WO | WO-2005/090165 A1 | 9/2005 |

\* cited by examiner

SHELVING SYSTEMS AND HOLDERS FOR FLEXIBLE BAGS FOR CONTAINING FLUID FOR USE IN FLUID DISPENSING SYSTEMS

BACKGROUND

1. Technical Field

An improved holder for supporting a flexible bag and enabling the bag to be connected to a pump of a multiple fluid dispensing system is disclosed. The holder enables the flexible bag to be supported in a vertical or substantially vertical position while the bag is connected to a pump. As a result, fluid within the bag is more effectively utilized with less waste. Shelving systems incorporating the enclosed holders and a fluid dispensing system incorporating the disclosed holders and shelving system are also disclosed.

2. Description of the Related Art

Multiple pump dispensing systems have been used in the paint industry. Specifically, a dispensing system incorporating multiple pumps dispensing viscous fluids, such as paint colorant, from flexible packages is disclosed in U.S. Pat. No. 6,273,298, owned by the assignee of the present application. Typically, such systems include piston pumps mounted on a rotary turntable with each pump coupled to the flexible package containing a viscous fluid, such as a colorant. The turntable, with the pumps and packages mounted thereon, is rotated until the desired pump and package is disposed over the container to be filled. A control system is utilized to rotate the table and control the amount of material dispensed from the packages by the pumps. Linear-type dispensing systems are also known.

Further, other paint dispensing systems are known wherein the pumps and flexible packages are stationary and the pumps are connected to a manifold by a plurality of hoses. In such a system, the container may also be stationary and disposed below the manifold or, in more advance systems such as that described in co-pending U.S. patent application Ser. No. 10/844,166, filed on May 12, 2004, the container may be held in a holder which pivots between a dispense and a closed position so that the nozzles passing through the manifold remain covered when the machine is not in use. Another type of design is disclosed in co-pending U.S. application Ser. No. 10/696,923 where the pumps and packages remain stationary with the pumps connected to a manifold and wherein the container is connected to a rotary turntable disposed below the manifold. The turntable is rotated until the container is in alignment with a nozzle in fluid communication with the desired flexible package. Ingredients are dispensed one at a time and the entire operation is controlled by a programmable controller. Application Ser. Nos. 10/844,166 and 10/696,923 are incorporated herein by reference.

Some currently available multiple fluid dispensers utilize nutating pumps and a computer control system to control the pumps. Nutating pumps have a piston which is positioned inside of a housing having a fluid inlet and a fluid outlet. The piston simultaneously slides axially and rotates inside of the housing. Existing nutating pumps can be operated by rotating the piston through a full 360° rotation and corresponding linear travel of the piston. The piston operation results in a specific amount of fluid pumped by the nutating pump with each revolution. Accordingly, the amount of fluid pumped for any given nutating pump is limited to multiples of the specific volume. If a smaller volume of fluid is desired, then a smaller sized nutating pump is used or manual calibration adjustments are made to the pump and controller.

For example, in paint colorants, a minimum dispense can be about 1/256th of a fluid ounce. U.S. Pat. Nos. 6,540,486 and 6,398,513 disclose improvements to nutating pump technology which provide for more accurate dispensing of paint colorants and other fluids such as hair dyes and cosmetics applications. Both of these patents are commonly assigned with this application and are incorporated herein by reference.

The multiple fluid dispensing technology originally developed for paint has found application in cosmetics, hair dye and food industries. For example, not all cosmetic products are universally applicable. Consumers having dry, oily or normal skin may require treatment products especially formulated for their particular condition. Hair products including shampoos, conditioners, hair dyes and permanent wave solutions are all quite sensitive to individual characteristics of the treated hair. No generic formula fits all types. Even more complicated are color cosmetics. A rainbow of shades are necessary to meet public demand. Stores find it a significant problem to stock all possible variations of a particular color cosmetic.

To address these problems, point of sale cosmetic dispensing machines have been developed. EP 0 443 741 discloses a formulation machine for preparing cosmetically functional products. The machine includes a plurality of containers for storing various cosmetic ingredients. An input mechanism is provided for entering into a computer specific criteria representative of a customer's needs. A series of instruction sets are then sent from the computer in response to the specific input criteria to a dispensing mechanism.

U.S. Pat. No. 4,871,262 describes an automatic cosmetic dispensing system for blending selected additives into a cosmetic base. A similar system is described in German Patent 41 10 299 with the further element of a facial sensor.

Other systems involve a skin analyzer for reading skin properties, a programmable device receiving the reading and correlating same with a foundation formula, and a formulation machine. Components of the formula held in a series of reservoirs within the machine are dosed into a receiving bottle and blended therein. These systems are described in U.S. Pat. Nos. 5,622,692 and 5,785,960. Because the systems disclosed in the '692 and '960 patents suffer from relatively poor precision, nutating pump technology was applied to improve the precision of the system as set forth in U.S. Pat. No. 6,510,366.

Certain problems are associated with the above-cited prior art in terms of the dispense functions. Specifically, the '692, '960 and '366 patents all dispense fluid through a single manifold disposed above the container or vial. As a result, specially designed and miniaturized nozzles and manifolds must be designed to accommodate the large variety of ingredients that may be used in any one cosmetics preparation. For high quality cosmetics products, to accommodate for a wide variety of skin types, a dispensing machine should preferably be able to accommodate an excess of twenty different ingredients even though only several ingredients may be used for a specific formula. Thus, the stationary manifold and nozzle design is impractical.

In the multiple fluid dispensing systems described above, the use of flexible bags for dispensing components such as colorants and dyes has become very popular. Manufacturers appreciate the bags because they are easy to fill and are relatively flat and therefore easy to package and ship. Retailers like the bags because they are compact and therefore easy to store. The bags have been previously used on rotary turntables as evidenced by U.S. Pat. No. 6,273,298.

The bags have also proven useful in stationary systems such as that illustrated in U.S. patent application Ser. No. 10/844,166.

However, there are certain drawbacks to currently available dispenser designs that dispense fluids contained in flexible bags. For example, U.S. Pat. No. 6,273,298 requires the use of a hard outer shell to properly support the bag on the turntable. The outer shell consumes space and adds to packaging costs. Further, the effective diameter of the turntable must be increased to accommodate for actuator levers used to mount and dismount the bags disposed within the outer shells.

One advancement over this design is found in application Ser. No. 10/844,166. However, in this design, the stationary bags are disposed horizontally, or lengthwise with the end wall of the bag that includes the outlet port being disposed relatively vertically and connected to the staggered pumps. In this design, when the bag is empty, a substantial quantity of fluid will be disposed along the lower side edge of the bag that rests on the bottom wall of the supporting tray or holder. Retailers have complained that this configuration results in substantial waste. On the other hand, the configuration disclosed in said application is extremely space efficient and therefore the machine itself is small enough to be suitable for retail environments.

Therefore, a new design is needed for a multiple dispensing system that takes advantage of the benefits provided by dispensing fluids from flexible bags but which overcomes the drawbacks of currently available designs and which still provides a space efficient design.

SUMMARY OF THE DISCLOSURE

In satisfaction of the aforenoted needs, an improved holder for supporting a flexible bag containing a viscous fluid is disclosed. The holder comprises a rear wall disposed between and connected to two sidewalls. The holder also includes a bottom wall connected to the rear wall and disposed between and connected to the sidewalls. The bottom wall and sidewalls define a u-shaped slot for receiving a cross beam through the bottom wall and into distal ends of the u-shaped slot disposed in the sidewalls so that the holder can pivot about an axis defined by the cross beam. The bottom wall also comprises a cut-out for accommodating the port of the flexible bag.

In a refinement, the holder has an open front for receiving the flexible bag. In a related refinement, the holder has an open top for receiving the flexible bag. In yet another related refinement, the holder has an open front and an open top for receiving the flexible bag.

In a refinement, an improved shelving system is disclosed for pivotally supporting flexible bags that contain fluid components and which have ports for connected to one of a plurality of pumps. The shelving system comprises a bottom plate connected to at least two spaced apart and upwardly extending rear tabs. The rear tabs are connected to and support a horizontal cross beam. The bottom plate comprises a plurality of spaced-apart openings with each opening providing access to an inlet of a pump. The system further comprises a plurality of holders pivotally mounted on the cross beam. Each holder comprises a rear wall disposed between and connected to two sidewalls and the bottom wall connected to the rear wall and disposed between and connected to the sidewalls. The bottom wall and sidewalls define a u-shaped slot for receiving the cross beam through the bottom wall and into the distal ends of the u-shaped slot in the sidewalls so that the holder can pivot about an axis defined by the cross beam. The bottom wall also includes a cut-out for accommodating the port of the flexible bag. The holder is able to pivot between and connected position where the cut-out or the bottom wall is in alignment with one of the openings in the bottom plate and the bottom wall is at least substantially horizontal and substantially parallel to the bottom plate so that the port of the bag can engage the inlet of the pump. The holder is also able to pivot to a disconnected position where the bottom wall of the holder is pivoted away from the bottom plate and the port of the bag is disconnected from the inlet of the pump.

In a refinement, the bottom surface of the bottom plate is connected to a plurality of spaced-apart brackets for supporting the pumps below the bottom plate with the inlets of the pumps extending up through the spaced-apart openings and the bottom plate.

In another refinement, the at least two upwardly extending rear tabs comprise a plurality of spaced apart tabs connected to the cross beam with openings between adjacent tabs for accommodating the holders and for permitting limited rearward pivotal movement of the holders.

In another refinement, each bag is disposed within a disposable box that is received in and supported by its respective holder.

In a further refinement, each holder has an open front, an open top or a combination of an open top and an open front.

An improved multiple fluid dispensing system is also disclosed which comprises a plurality of flexible bags, each bag containing a fluid and having a port for connecting to one of a plurality of pumps. Each pump has an inlet nozzle for insertion into the port of one of the bags. The bags and the pumps are supported by at least one shelving system that comprises a bottom plate connected to at least two spaced apart and upwardly extending rear tabs. The rear tabs are connected to a horizontal cross beam. The bottom plate comprises a plurality of spaced-apart openings with each opening providing access to an inlet nozzle of one of the pumps. The system also comprises a plurality of holders with each holder holding one of the bags and being pivotally mounted on the cross beam and in alignment with one of the openings in the bottom plate. Each holder comprises a rear wall disposed between and connected to two sidewalls and a bottom wall connected to the rear wall and disposed between and connected to the sidewalls. The bottom wall and sidewalls defining a u-shaped slot for receiving the cross beam through the bottom wall and into distal ends of the u-shaped slot disposed in the sidewalls so that the holder can pivot about an axis defined by the cross beam. The bottom wall also comprises a cut-out for accommodating the port of its respective flexible bag. The holders are able to pivot between and connected position where the cut-out of the bottom wall is in alignment with one of the openings in the bottom plate and the port of the bag engages the inlet of the pump that extends up through the opening of the bottom plate as well as a disconnected position where the bottom wall of the holder is pivoted away from the bottom plate and the port of the bag is disconnected from the inlet of the pump.

In a refinement, the pumps are connected to a bottom surface of the bottom plate by a plurality of spaced-apart brackets. As an alternative, the pumps may be connected to a single bracket which, in turn, are connected to a bottom surface of the bottom plate. As yet another alternative, the pumps may be directly connected to the bottom surface of the bottom plate.

In a refinement, the at least two tabs comprise a series of spaced-apart tabs that extend upward from the bottom plate and which define openings between two adjacent tabs for accommodating the holder and permitting limited pivotal movement of the holders while they are mounted on the cross bar.

The port of a typical flexible bag passes through a pair of spaced-apart and parallel flanges with a short, rigid conduit connecting the flanges. In a refinement, the pair of spaced-apart flanges of the port of the bag are sandwiched between the bottom wall of the holder and the bottom plate of the shelving system when the holder is pivoted upward into the connected position where the port of the bag is forced over the inlet nozzle of the pump.

It will be also noted that, in this connected position, the bag is in a vertical configuration with the shorter bottom edge of the bag that includes the port being disposed and resting along the bottom wall of the holder and with the longer side edges of the bag extending upward within the holder. As a result, less fluid is disposed along the longer side edges when the bag becomes near-empty and the system is able to dispense a higher percentage of the fluid contained within the bag.

Other features and advantages of the disclosed holders, shelving systems and dispensing systems will be apparent upon reading the following detailed description and appended claims, with reference to the accompanying drawings.

BRIEF DESCRIPTION OF THE DRAWINGS

The disclosed holders, shelving systems and dispensing systems and methods of use thereof are described more or less diagrammatically in the accompanying drawings, wherein.

It should be understood that the drawings are not necessarily to scale and that the embodiments are sometimes illustrated by phantom lines, diagrammatic representations and fragmentary views. In certain instances, details may have been omitted which are not necessary for an understanding of the disclosed holders, shelving systems or dispensing systems which render other details difficult to perceive. It should be understood, of course, that this disclosure is not necessarily limited to the particular embodiments illustrated herein.

DETAILED DESCRIPTION OF THE PRESENTLY PREFERRED EMBODIMENTS

Figure 1:
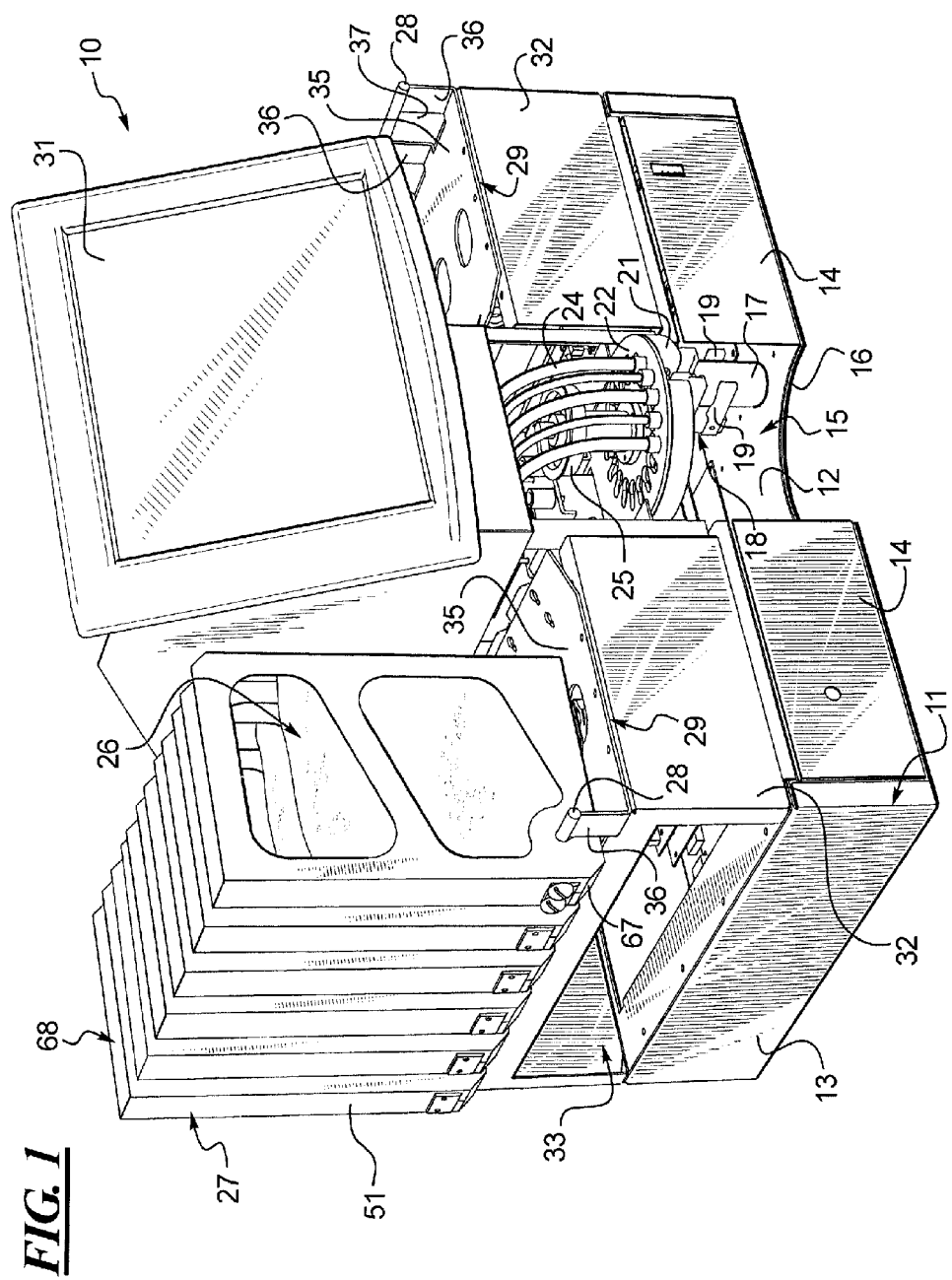
FIG. 1 is a perspective view of an improved fluid dispensing system made in accordance with this disclosure that efficiently utilizes fluid components disposed in flexible bags.

Turning first to FIG. 1, a dispensing system 10 is illustrated. The system 10 includes a lower base structure 11 including a bottom panel 12 connected to sidewalls 13 and which optionally can include a pair of drawers shown at 14. The base 11 provides a sufficient amount of open space shown generally at 15 (see also the recess 16 in the bottom panel 12) for the mounting of a container 17 on a holder 18 that includes a pair of forked legs 19. The container 17 and holder 18 are mounted beneath a rotary turntable 21. The rotary turntable 21 is supported beneath a manifold plate 22 which, in turn, includes a plurality of openings 23 for accommodating hoses 24 and nozzles (not shown). During a dispense, a controller (not shown) activates the motor 25 to rotate the turntable 21 so that the container 17 is in alignment with the hose 24 and nozzle (not shown) connected to the ingredient bag 26 containing the material currently being dispensed. Because this disclosure is directed primarily at the bag holders 27, the upright configuration of the bags 26 and holders 27 when in the connected position and the employment of the cross bars 28 of the supporting bracket 29, the operation of the controller (not shown) and the touch screen 31 will not be described in detail here.

Details regarding the design and operation of similar devices can be found in co-pending U.S. patent application Ser. Nos. 10/693,923 and 10/844,166, both of which are incorporated herein by reference.

As shown in FIG. 1, the system 10 includes two brackets 29 on either side of the touch screen 31 which can accommodate a row of holders 27 for supporting flexible ingredient bags 26. Each bracket 29 is mounted on top of its own supporting frame 32 which, as shown at the left in FIG. 1 includes a lower open space 33 for accommodating the pumps shown at 34 in FIGS. 2 and 3.

The brackets 29 include bottom plates 35 which are connected to upwardly extending rear tabs 36 which are connected to and support the cross bar 28. As shown in the right side in FIG. 1, the tabs 36 are preferably spaced apart to provide an opening 37 between adjacent tabs 36 (see the right side of FIG. 1) which accommodates a holder 27 (see the left side of FIG. 1).

Figure 2:
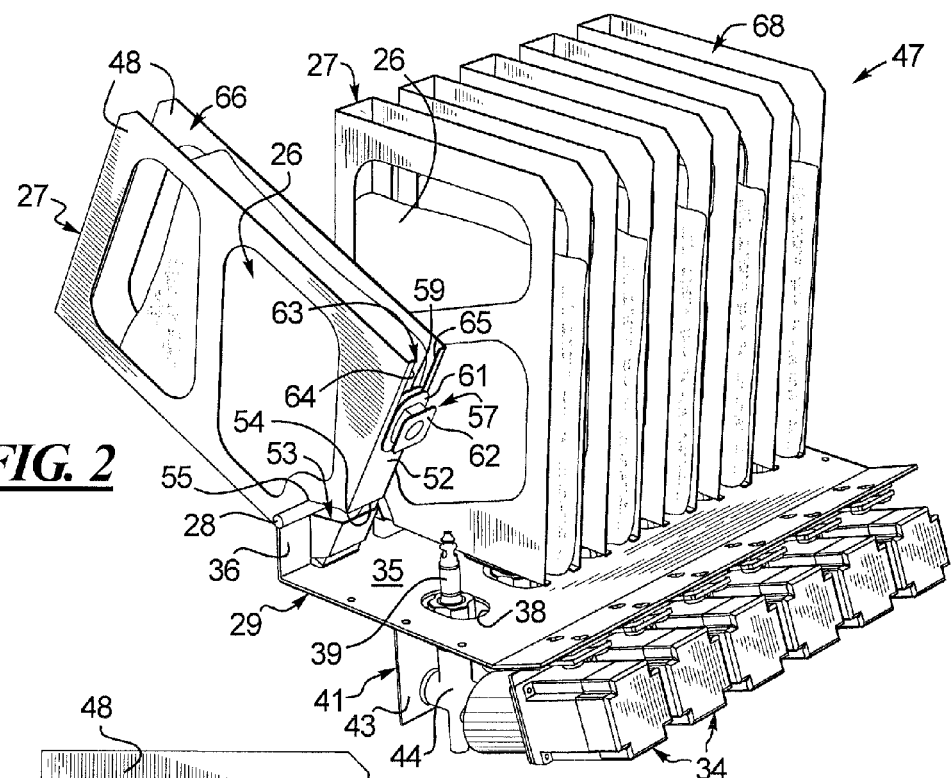
FIG. 2 is a partial perspective view of the fluid dispensing system shown in FIG. 1 particularly illustrating the pivotal movement of one holder and bag from a connected position to a disconnected position.

As shown in FIG. 2, the spaces 37 which accommodate a holder 27 enable the holders 27 to pivot rearwardly away from the bottom plate 35 to disconnect a bag 26 from its respective pump 34 as shown in FIG. 2. Still referring to FIG. 2, the bottom plate 35 includes a plurality of spaced-apart openings 38 which accommodate an inlet or, more specifically, an inlet nozzle 39 of each pump 34. As shown in FIG. 2, one preferred design includes a separate bracket 41 for mounting each pump 34 to the underside 42 of the bottom plate 35. The brackets 41 can be a simple L-configuration with a vertical leg 43 attached to the pump housing 44 and a horizontal leg 45 secured to the underside 42 of the bottom plate 35. Alternative arrangements include directly connecting the pumps 34 to the bottom plate 35 or including a single bracket 41 for an entire row of pumps 34. Also, the pumps may be supported by a structure not connected to or directly associated with the shelving system 47 shown in FIG. 2.

Figure 3:
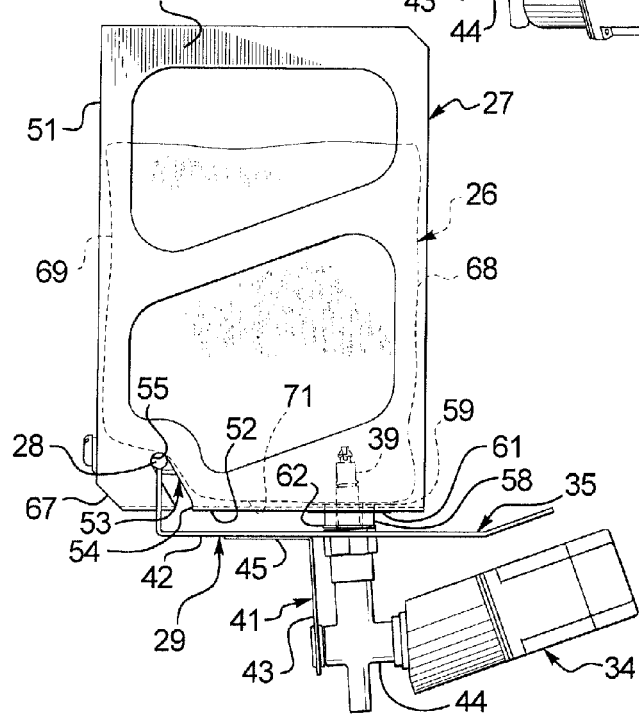
FIG. 3 is a side plan view of a single holder, bag and pump as connected to and supported by the bottom plate and cross beam of the disclosed design.

As shown in FIGS. 2 and 3, each holder 27 includes a pair of sidewalls 48 which are connected to a rear wall 51. The rear wall 51 supports the bag 26 when the holder 27 is tilted backward into the disconnected position shown on the left side at FIG. 2. The rear wall 51 may or may not be directly connected to a bottom wall 52. The bottom wall 52 and the opposing sidewalls 48 define a u-shaped slot 53 which has an opening 54 that passes through the bottom wall 52 and extends into the sidewalls 48 and terminates at two opposing distal ends 55 disposed in the sidewalls 48 as shown in FIGS. 2 and 3. The distal ends 55 of the u-shaped slot 53 accommodate the cross bar 28 and enable the holders 27 to pivot between the position shown in FIG. 2 and FIG. 3. The use of the spaced-apart rear tabs 36 of the supporting bracket 29 facilitates the alignment of the port 57 of the bag 26 with its respective pump inlet nozzle 39 as shown in FIG. 2.

The port 57 of each bag 26 includes a solid outlet conduit 58 that passes through and is connected to three flanges including an inner flange 59, a middle flange 61 and an outer flange 62. The inner and middle flanges 59, 61 define a slot which is received in the cut-out 63 disposed the bottom wall 52 of the holder 27 as best seen in FIG. 2. To insert the bag 26 in the holder 27, the flanges 59, 61 are aligned with the opposing edges 64, 65 that define the cut-out 63 in the bottom wall 52 and the bag 26 is slid into the position as shown in FIG. 2. With the use of such a cut-out 63, the holder 27 preferably include an open front end 66. Further, because the rearward pivotal movement of each holder 27 is limited by engagement of the lower heel 67 against the bottom plate 35 as shown in FIG. 2, a top panel for the holder 27 is not necessary and therefore an open top end 68 is preferred to save material, costs and weight.

As shown in FIG. 3, the bag 26 is supported in an upright position so that the longer side edges 68, 69 of the bag 26 are disposed in a vertical orientation when in the connected position as shown in FIGS. 1 and 3. As a result, only a portion of the lower and narrower bottom edge 71 is disposed in a horizontal position when in a connected position is shown in FIG. 3. Further, the engagement of the cross bar 28 with the bottom edge 71 of the bag 26 further limits the actual length of the bag 26 that is disposed in the lower horizontal position as shown in FIG. 3 when the holder 27 and bag 26 are disposed in the upright and connected position. In this way, only a minor amount of the liquid components originally contained within the bag will be trapped along the lower edge 71 and therefore unable to be withdrawn through the nozzle 39 as the bag nears an empty state. In contrast to other designs where the long site at 68 is disposed horizontally or near horizontally when the bag 26 is in a dispensed position, less material is wasted. In short, providing an upright configuration uses the material contained within the bags 26 in a more efficient manner and produces less waste.

While only certain embodiments have been set forth, alternative embodiments and various modifications will be apparent from the above description to those skilled in the art. These and other alternatives are considered equivalents and within the spirit and scope of this disclosure.

What is claimed is:

1. A shelving system for pivotally supporting flexible bags containing fluid components and having ports for connecting to one of a plurality of pumps, the shelving system comprising:
   a bottom plate connected at least two spaced-apart upwardly extending rear tabs, interface, by which a user can cause the control mechanism to switch between the first setting and the second setting
   the bottom plate comprising a plurality of space-apart openings, each opening for providing access to an inlet of a pump,
   a plurality of holders pivotally mounted on the cross beam, each holder comprising
   a rear wall disposed between and connected to two side walls,
   a bottom wall disposed between and connected to the side walls,
   the bottom wall and side walls defining a u-shaped slot for receiving the cross beam through the bottom wall and into distal ends of the u-shaped slot disposed in the side walls so that the holder can pivot about an axis defined by the cross beam,
   the bottom wall also comprising a cut-out for accommodating the port of the flexible bag,
   the holder being able to pivot between a connected position where the cut-out of bottom wall is in alignment with one openings in the bottom plate and the bottom wall is at least substantially horizontal and substantially parallel to the bottom plate so that the port of the bag can engage the inlet of a pump and a disconnected position where the bottom wall is pivoted away from the bottom plate.

2. The shelving system of claim 1 wherein the a bottom surface of the bottom plate is connected to a plurality of spaced-apart brackets for supporting the pumps below the bottom plate with inlets of the pumps extending up through the spaced-apart openings in the bottom plate.

3. The shelving system of claim 1 wherein the at least two tabs comprises a plurality of spaced-apart rear tabs connected to the cross beam with openings between adjacent tabs for accommodating the holders and for permitting limited rearward pivotal movement of the holders.

4. The shelving system of claim 1 wherein each bag is disposed within a box that is received in and supported by its respective holder.

5. The shelving system of claim 1 wherein each holder has an open front for receiving the flexible bag.

6. The shelving system of claim 1 wherein each holder has an open top for receiving the flexible bag.

7. The shelving system of claim 1 wherein each holder has an open top and an open front for receiving the flexible bag.

8. A multiple fluid dispensing system comprising:
   a plurality of flexible bags each bag containing a fluid and having a port for connecting to one of a plurality of pumps, each of the pumps having an inlet nozzle for insertion into a port of one of the bags, the bags and pumps being supported by at least one shelving system comprising
   a bottom plate connected at least two spaced-apart upwardly extending rear tabs,
   the rear tabs being connected to a horizontal cross beam,
   the bottom plate comprising a plurality of spaced-apart openings, each opening for providing access to an inlet nozzle of one the pumps,
   a plurality of holders, each holder for holding one of the bags and being pivotally mounted on the cross beam and in alignment with one of the openings in the bottom plate, each holder comprising
   a rear wall disposed between and connected to two side walls,
   a bottom wall disposed between and connected to the side walls,
   the bottom wall and side walls defining a u-shaped slot for receiving the cross beam through the bottom wall and into distal ends of the u-shaped slot disposed in the side walls so that the holder can pivot about an axis defined by the cross beam,
   the bottom wall also comprising a cut-out for accommodating the port of the flexible bag,
   the holders being able to pivot between a connected position where the cut-out of bottom wall is in alignment with one openings in the bottom plate and the port of the bag in the holder engages the inlet of the pump that extends up through the opening in the bottom plate and a disconnected position where the bottom wall at the holder is pivoted away from the bottom plate and the port of the bag is disconnected from the inlet of the pump.

9. The dispensing system of claim 8 wherein the a bottom surface of the bottom plate is connected to a plurality of spaced apart brackets for supporting the pumps below the bottom plate with inlets of the pumps extending up through the spaced-apart openings in the bottom plate.

10. The dispensing system of claim 8 wherein the at least two tabs comprises a plurality of spaced apart rear tabs with openings between adjacent tabs for accommodating the holders and for permitting limited rearward pivotal movement of the holders.

11. The dispensing system of claim 8 wherein each bag is disposed within a box that is received in and supported by the holders.

12. The dispensing system of claim 8 wherein each holder has an open front for receiving the flexible bag.

13. The dispensing system of claim 8 wherein each holder has an open top for receiving the flexible bag.

14. The dispensing system of claim 8 wherein each holder has an open top and an open front for receiving the flexible bag.

15. The dispensing system of claim 8 wherein the port of each bag comprises a rigid conduit disposed between and connected to three spaced-apart and parallel flanges including an inner flange, a middle flange and an outer flange, the middle and outer flanges being sandwiched between the bottom wall of the holder and the bottom plate when the holder and bag are in a dispense position, and portions of the bottom wall of the holder being sandwiched between the inner and middle flanges when the bag is inserted into the holder.

* * * * *

UNITED STATES PATENT AND TRADEMARK OFFICE
CERTIFICATE OF CORRECTION

PATENT NO. : 7,320,416 B2 Page 1 of 1
APPLICATION NO. : 11/114371
DATED : January 22, 2008
INVENTOR(S) : Miller et al.

It is certified that error appears in the above-identified patent and that said Letters Patent is hereby corrected as shown below:

Column 8, Line 67: replace "apait" with --apart--

Signed and Sealed this

Second Day of December, 2008

JON W. DUDAS
*Director of the United States Patent and Trademark Office*